US009327136B2

(12) United States Patent
Hedgecock

(10) Patent No.: US 9,327,136 B2
(45) Date of Patent: May 3, 2016

(54) SPIRAL MAGNETIC VORTEX INSTRUMENT

(71) Applicant: Sean Hedgecock, Tiburon, CA (US)

(72) Inventor: Sean Hedgecock, Tiburon, CA (US)

(73) Assignee: E-MERGENCE TECHNOLOGIES, INC., Corte Madera, CA (US)

( * ) Notice: Subject to any disclaimer, the term of this patent is extended or adjusted under 35 U.S.C. 154(b) by 176 days.

(21) Appl. No.: 14/038,753

(22) Filed: Sep. 27, 2013

(65) Prior Publication Data

US 2014/0088337 A1   Mar. 27, 2014

Related U.S. Application Data

(60) Provisional application No. 61/706,682, filed on Sep. 27, 2012.

(51) Int. Cl.
*A61N 2/12* (2006.01)
*A61N 2/06* (2006.01)
*A61N 2/00* (2006.01)

(52) U.S. Cl.
CPC .. *A61N 2/12* (2013.01); *A61N 2/06* (2013.01); *A61N 2/008* (2013.01)

(58) Field of Classification Search
CPC ................................. A61N 2/12; A61N 2/008
USPC ........................................................ 600/9, 15
See application file for complete search history.

(56) References Cited

U.S. PATENT DOCUMENTS 4,764,743 A * 8/1988 Leupold et al. ............... 335/306
6,123,657 A * 9/2000 Ishikawa et al. .................. 600/9

* cited by examiner

*Primary Examiner* — Navin Natnithithadha
*Assistant Examiner* — Kaylee Wilson
(74) *Attorney, Agent, or Firm* — Mathew J. Temmerman; Temmerman Law Office

(57) ABSTRACT

A magnetic device for magnetic therapy, the device comprising a magnetic drum having an inner surface and an outer surface, a plurality of permanent magnets, a hollow safety sleeve, and an electric motor for powering the magnetic device by means of a power source. The plurality of permanent magnets is positioned on the inner surface of the magnetic drum so as to form a helical pattern thereon. The magnetic drum is positioned in the hollow safety sleeve and connected to an output shaft of the electric motor by means of a plurality of bearings. The electric motor rotates the magnetic drum and the plurality of permanent magnets to produce an oscillating magnetic field for use in magnetic therapy.

20 Claims, 4 Drawing Sheets

SPIRAL MAGNETIC VORTEX INSTRUMENT

RELATED APPLICATIONS

This application claims priority from the U.S. provisional application with Ser. No. 61/706,682, which was filed on Sep. 27, 2012. The disclosure of that provisional application is incorporated herein as if set out in full.

BACKGROUND OF THE DISCLOSURE

1. Technical Field of the Disclosure

The present embodiment relates in general to electromagnetic technology. More specifically, the present embodiment relates to a device that uses electromagnetic technology to benefit human health.

2. Description of the Related Art

The human body is largely composed of water, and electromagnetic energy pulses run through the body. At a physical level all matter is simply a form of energy and is governed in part by the subtle energy fields that are around them. The human body is simply one other form of matter, and hence is influenced by these magnetic fields. Magnetic fields are known to improve blood flow in the tissues when applied. Although this knowledge has been expressed historically through indigenous and enlightened cultures, it has also recently been proven through scientific processes.

Magnetic therapy refers to the use of placing static magnets directly on the body, generally over regions of pain. Magnetic therapy devices employ safe and non-invasive methods of applying magnetic fields to a body for therapeutic purposes. These devices accelerate the natural healing process of the body and provide natural pain relief without any adverse side effects. Electromagnetic forces have a significant effect on human health and can stimulate the metabolism of the cells that make up the human tissues. In the past, various methods such as bandaging, massages, injections and drug treatments have been used in an attempt to promote better circulation and blood supply to the tissue. This can now be achieved entirely without side effects by the application of deep penetrating, alternating magnetic fields. Magnetic therapy is one of the oldest forms of natural healing, whose main effect is to activate the body's own defensive forces, improve cellular metabolism and increase the intake of oxygen by the tissue. The application of magnetic fields improves the blood circulation by causing blood vessels to dilate and increases the oxygen content in the blood.

Therapeutic magnets traditionally come in two different types of polarity arrangements. They are unipolar magnets and bipolar or alternating-pole magnets. Magnets that have north on one side and south on the other are known as unipolar magnets. Bipolar or alternating-pole magnets are made from a sheet of magnetic material with north and south magnets arranged in an alternating pattern, so that both north and south face the skin.

Conventional magnetic therapy devices include magnetic straps for wrists, ankles, knees, and the back. These devices are also available as shoe insoles, mattresses, magnetic blankets having magnets woven into the material, magnetic creams, magnetic supplements, plasters/patches and water that have been "magnetized". These magnetic therapy devices have been shown to improve blood flow in underlying tissues.

Pulsed electromagnetic field therapy (PEMFT) is quite distinct from true magnet therapy. Pulsed electromagnetic field therapy is a reparative technique most commonly used in the field of orthopedics for the treatment of non-union fractures, failed fusions, congenital pseudarthrosis and depression. In the case of bone healing, PEMFT uses electrical energy to direct a series of magnetic pulses through injured tissue whereby each magnetic pulse induces a tiny electrical signal that stimulates cellular repair. Many studies have also demonstrated the effectiveness of PEMFT in healing soft-tissue wounds, suppressing inflammatory responses at the cell membrane level to alleviate pain, and increasing range of motion and had shown effective for osteoarthritis, stress, incontinence, multiple sclerosis and possibly other conditions as well. Pulsed magnetic fields can accelerate the healing process when applied across the site of a bone fracture. Pulsed electromagnetic fields are utilized to enhance tissue repair in mammals and were also used to stimulate the growth of stem cells. PEMFT may be further utilized to treat severe depression if the patient failed to respond to antidepressants. This treatment, known as transcranial pulsed electromagnetic therapy uses a strong electromagnetic field that is pulsed into the patient's head.

Repetitive transcranial magnetic stimulation (rTMS) is more closely related to standard magnet therapy. It involves applying low-frequency magnetic pulses to the brain. rTMS has been investigated for treating emotional illnesses and other conditions that originate in the brain. The results of preliminary studies have been generally promising.

While modern western culture and science have used magnetism in the field of health care such as in magnetic resonance imaging (MRI) machines, still modern western culture as of this writing has yet to capitalize and leverage this knowledge of the effects of electromagnetism on healthcare and wellness in a widely accessible way.

Recent advancements in the art provide a magnetic therapy device that affects a compression of multiple magnetic fields by rapid rotation of aligned permanent magnets in relation to corresponding fixed multiple magnetic fields. In this device an opposing multiple magnetic polar field is established and positioned in a spaced relation to the rotating magnetic field, thereby imparting a therapeutic compression effect of magnetic fields on a biological entity positioned within the fields. However, this assembly provides only opposing multiple magnetic fields and must be carefully positioned in spaced relation to the rotating magnetic field to impart the desired therapeutic effect.

One of the existing systems provides a bi-axial rotating magnetic therapeutic device, comprising a magnetic unit that is made to rotate about two separate axes at the same time housed within non-magnetic components. One axis of rotation is in the direction of a rod mounted to the magnet, and the other axis is along an imaginary line that runs through the center of the magnetic body, roughly perpendicular to the rod. The two rotational movements of the magnet produce both a time-varying field of magnetic flux density and a time-varying field of angular flux displacement. The main drawback of this system is that the device has a complex structure and the two rotational movements of the magnet produce only perpendicular magnetic fields, which do not provide the desired medical effect.

Another existing system discloses a magnetic therapy device that includes a power source, a motor, a tachometer, and a microprocessor. The power source may be configured to supply power to the motor, which controls the disk mounted with a plurality of magnets. The tachometer is configured to monitor the magnetic field generated by the plurality of magnets and provides a signal to a microprocessor based on the monitored magnetic field. The microprocessor may be configured to control the motor based on the signal received from the tachometer. The downside to this system is that the magnetic field thus generated is not constant thereby causing a pulsating effect on the affected body part.

As can be seen, there is a need for a device for magnetic therapy that assists with the healing processes of the human body. There is a further need for a device that is inexpensive, simple in construction, environmentally friendly and provides a constant magnetic field that can be applied for therapeutic purposes. The present invention overcomes the prior art shortcomings by accomplishing these objectives.

SUMMARY OF THE DISCLOSURE

To minimize the limitations found in the prior art and to minimize other limitations that will be apparent upon the reading of the specifications, the preferred embodiment of the present invention provides a magnetic therapeutic device that uses electromagnetic technology to benefit human health.

In a preferred embodiment the invention comprises a spiral magnetic therapeutic device that generates an oscillating magnetic field that assists with the self-healing processes in the human body. The present invention is based on the principle of spinning permanent rare earth magnets creating an oscillating magnetic field. The spiral magnetic therapeutic device comprises an electric motor, a safety sleeve, a magnetic drum, a plurality of permanent magnets and a power source. The safety sleeve has a substantially hollow substantially cylindrical shape, which is affixed to the electric motor by means of a safety sleeve mount. The magnetic drum has an inner surface and an outer surface, of which the inner surface faces a central axis running longitudinally through the safety sleeve. The magnetic drum is free to rotate when energized from the power source. The plurality of permanent magnets is positioned in a helical pattern on the inner surface of the magnetic drum. The magnetic drum is inserted into the safety sleeve and connected to an output shaft of the electric motor by means of a plurality of bearings. The power source turns on the electric motor to rotate the magnetic drum embedded with the plurality of permanent magnets so as to produce an oscillating magnetic field that creates a vortex around the matter it faces. The design of the present invention is predicated on a helix of the plurality of permanent magnets arranged at a certain angle or twist that generates a rapidly oscillating magnetic field.

A first objective of the present invention is to provide a magnetic therapeutic device that provides an inexpensive, non-invasive, environmentally friendly, and non-toxic compliment to conventional medical care.

A second objective of the present invention is to provide a magnetic therapeutic device that is portable, inexpensive, and widely accessible.

A third objective of the present invention is to provide a non-electrified, passive magnetic field that may be applied to the human body.

A fourth objective of the present invention is to provide a magnetic therapeutic device that creates a more subtle, stable, and natural magnetic field that increases the body's ability to work with less stresses and enhances the ability to heal and work efficiently.

Another objective of the present invention is to assist with the self-healing processes in the human body.

Yet another objective of the invention is to provide an oscillating magnetic field that creates a vortex to benefit human health.

Still another objective of the invention is to provide a device as a remedy for pain management, DNA-based disorders, wound healing, autoimmune disorders, sports medicine, addiction, anxiety, depression, wellness and anti-aging.

These and other advantages and features of the present invention are described with specificity so as to make the present invention understandable to one of ordinary skill in the art.

BRIEF DESCRIPTION OF THE DRAWINGS

In order to enhance their clarity and improve understanding of these various elements and embodiments of the invention, elements in the figures have not necessarily been drawn to scale. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below. Finally, many of the steps are presented below in an order intended only as an exemplary embodiment. Unless logically required, no step should be assumed to be required earlier in the process than a later step simply because it is written first in this document.

Figure 1:
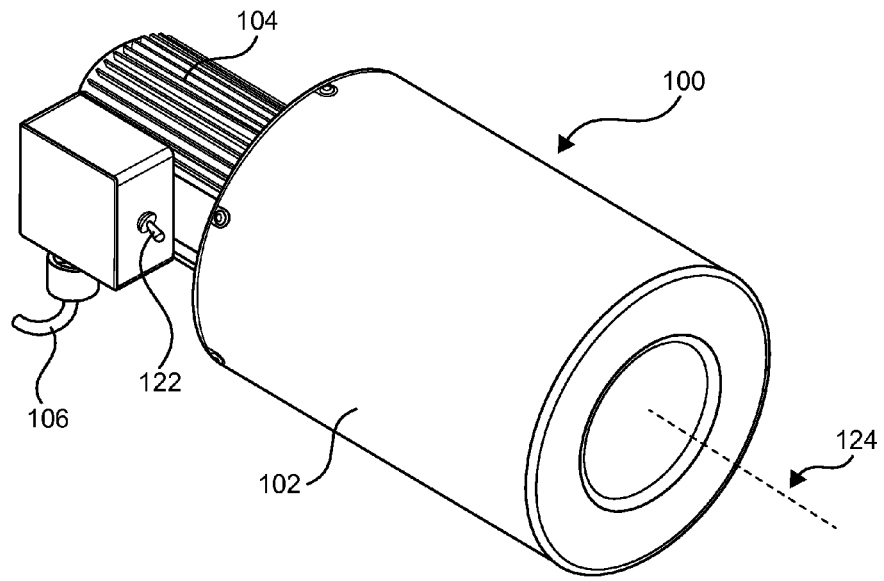
FIG. 1 illustrates a perspective view of a spiral magnetic therapeutic device according to a preferred embodiment of the present invention.
Figure 2:
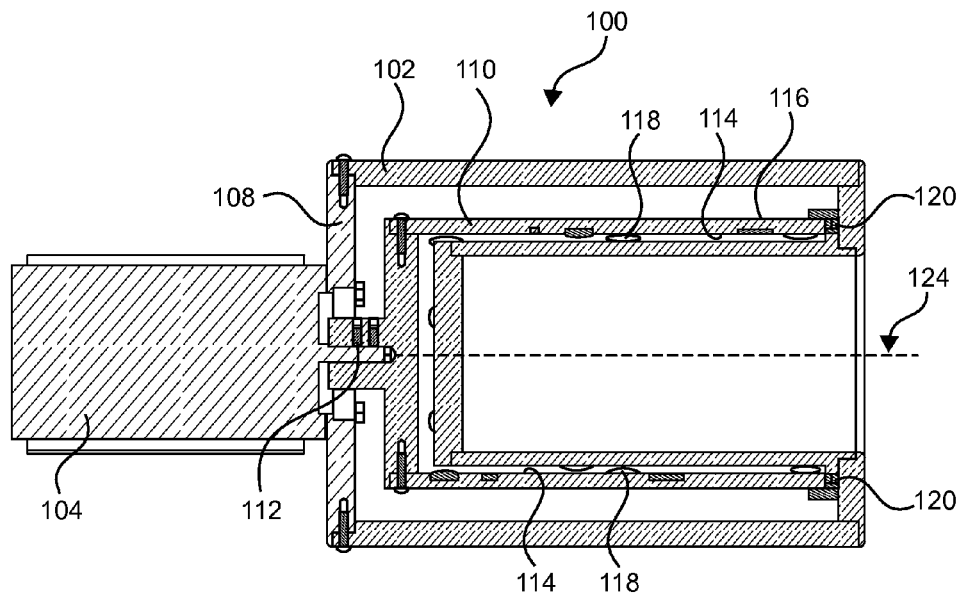
FIG. 2 illustrates a cross-sectional view of the spiral magnetic therapeutic device along a central line according to the preferred embodiment of the present invention.

Referring to FIG. 1 and FIG. 2, a spiral magnetic therapeutic device 100 and the cross-sectional view according to a preferred embodiment of the present invention is illustrated. The spiral magnetic therapeutic device 100 comprises a magnetic drum 110, a plurality of permanent magnets 118, a hollow safety sleeve 102, an electric motor 104 and a power source 106 to turn on the electric motor 104 by means of an ON/OFF switch 122. The magnetic drum 110 is substantially cylindrical in shape having an inner surface 114 and an outer surface 116, with a plurality of slots 126 (see FIG. 7A) on the inner surface 114. The plurality of permanent magnets 118 is positioned or counter sunk into the plurality of slots 126 (see FIG. 7A) on the inner surface 114 of the magnetic drum 110 to form a helical pattern. The hollow safety sleeve 102, substantially cylindrical in shape, houses the magnetic drum 110 having the plurality of permanent magnets 118. The magnetic drum 110 is connected to an output shaft 112 of the electric motor 104 by means of a plurality of bearings 120, and the hollow safety sleeve 102 is attached to the electric motor 104 by means of a safety sleeve mount 108. The magnetic drum 110 is free to rotate when energized from the power source 106. The plurality of permanent magnets 118 faces a central axis 124 running longitudinally through the safety sleeve 102. The spiral magnetic therapeutic device 100 works on the principle of spinning permanent rare earth magnets to create an oscillating magnetic field. The plurality of permanent magnets 118 are rare earth permanent magnets selected from a group consisting of: neodymium ($Nd_2Fe_{14}B$), samarium-cobalt ($SmCo_5$), Alnico, Sr-ferrite, Sm(Co, Fe, Cu, Zr) and other suitable permanent magnets.

When power is applied to the spiral magnetic device 100 by means of the ON/OFF switch 122, the electric motor 104 rotates the magnetic drum 110 having the plurality of permanent magnets 118 to produce an oscillating magnetic field, thereby creating a vortex around the matter to benefit human health. The electric motor 104 may be powered from an AC power source or a DC power source. The normal rotational speed of the magnetic drum 110 is substantially constant. Each of the plurality of permanent magnets 118 is oriented in the same direction either all with the north pole facing the central axis 124 or all with the south pole facing the central axis 124 and has a high remanence value (remanent magnetization) such as at least 0.5 T and preferably at least 0.8 T. The safety sleeve 102 of the device 100 can be of any shape and dimension to protect a user from the spinning magnetic drum 110 and the plurality of permanent magnets 118. The plurality of permanent magnets 118 is arranged at a certain angle or twist to form a helix. When the electric motor 104 is turned on, the magnetic drum 110 rotates, thereby generating a magnetic field of approximately 140 tesla. The magnetic field creates a vortex around the matter near to the device 100 within a space of approximately 5 to 10 square feet. Theoretically, the magnetic field puts a positive charge and a negative charge around matter at a cellular level, causing matter to fall into designed or proper realignment. This concept of magnetic fields is used to benefit health care of humans.

Figure 3:
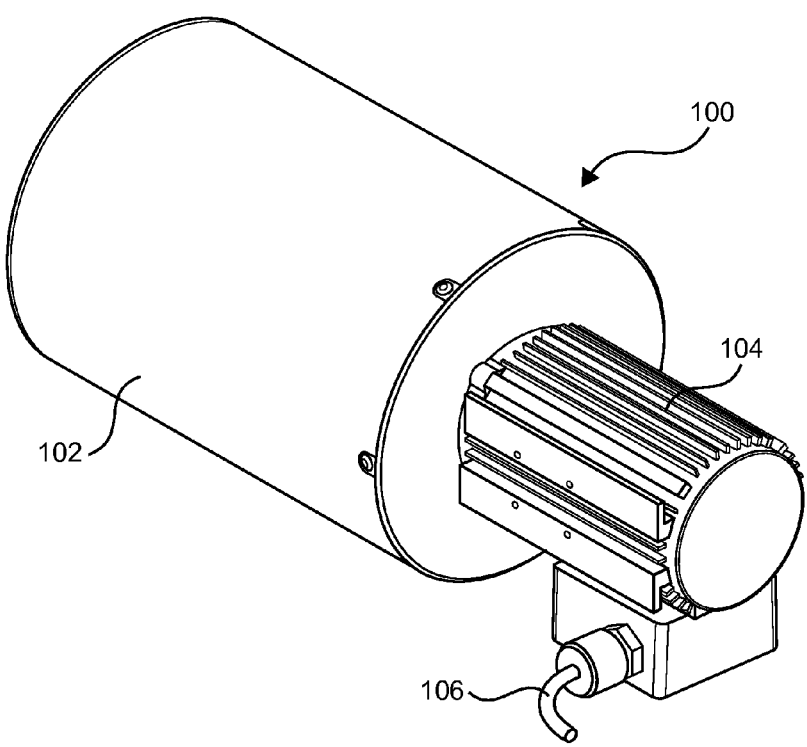
FIG. 3 illustrates a perspective view of the spiral magnetic therapeutic device according to the preferred embodiment of the present invention.

FIG. 3 illustrates a perspective view of the spiral magnetic therapeutic device 100 according to the preferred embodiment of the present invention. The electric motor 104 is connected to the safety sleeve 102 by means of the safety sleeve mount 108. The safety sleeve 102 may be of any shape and dimension to protect a user from the spinning magnetic drum 110 and the plurality of permanent magnets 118. The electric motor 104 of the device 100 can be powered by an AC supply or a DC supply. In normal operation the rotational speed of the magnetic drum 110 is substantially constant. The rotational speed can also increase from a few rpm to as high as 5000 rpm.

Figure 4:
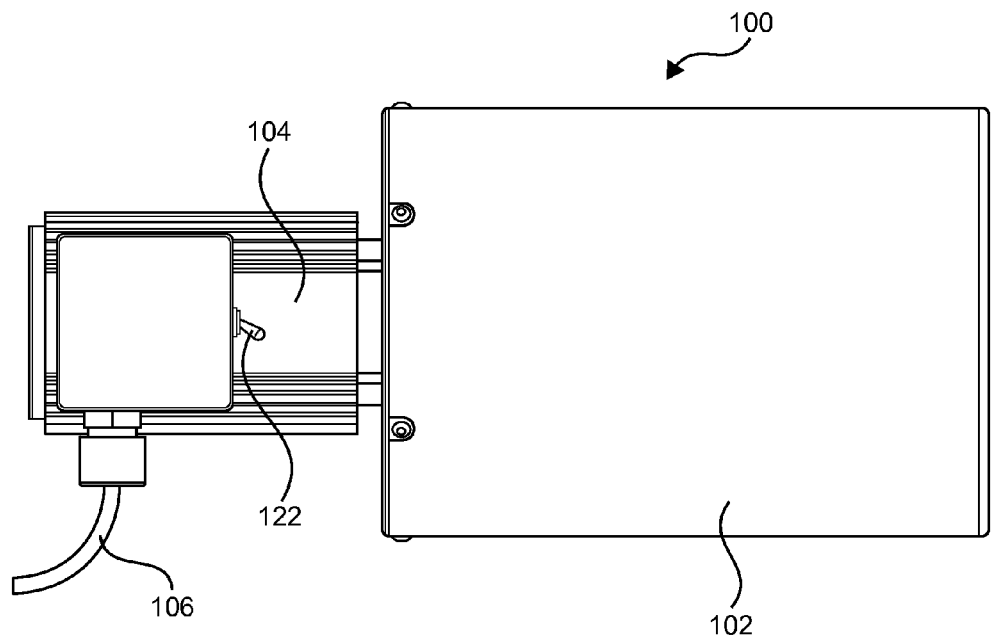
FIG. 4 illustrates a right perspective view of the spiral magnetic therapeutic device according to the preferred embodiment of the present invention.

FIG. 4 illustrates a right perspective view of the spiral magnetic therapeutic device 100 according to the preferred embodiment of the present invention. The ON/OFF switch 122 turns on the power supply 106 of the device 100. As the power supply 106 is turned on, the electric motor 104 is activated, which rotates the magnetic drum 110. An oscillating magnetic field is produced by the spinning of the plurality of permanent magnets 118. The oscillating magnetic field puts a positive and negative charge around matter at a cellular level, causing matter to fall into designed or proper realignment. The magnetic field can be utilized for medical application that optimizes the body's innate ability to heal itself.

Figure 5A:
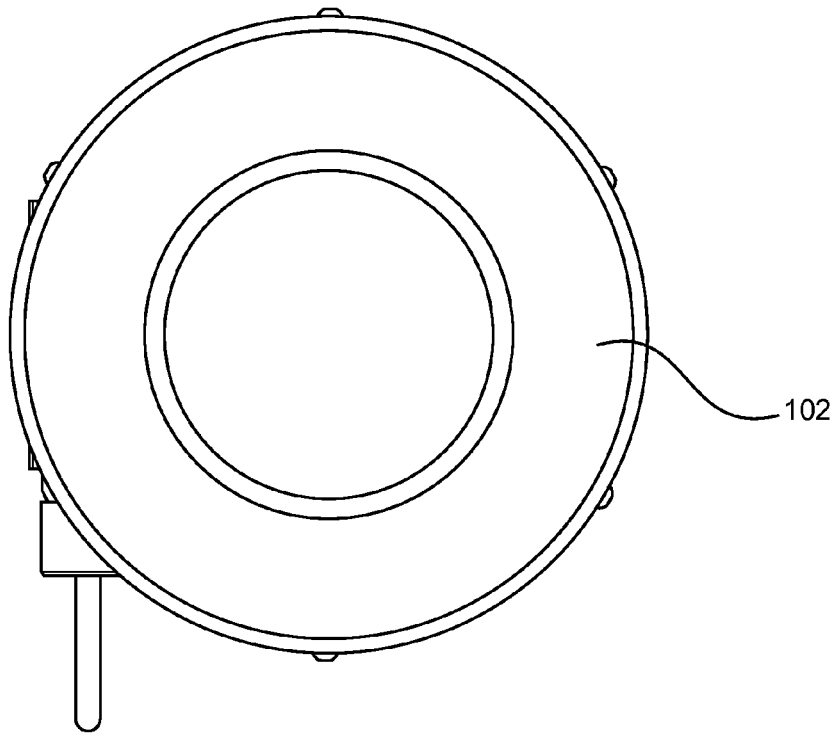
FIG. 5A-5B illustrates a front view and a rear view of the spiral magnetic therapeutic device according to the preferred embodiment of the present invention.
Figure 5B:
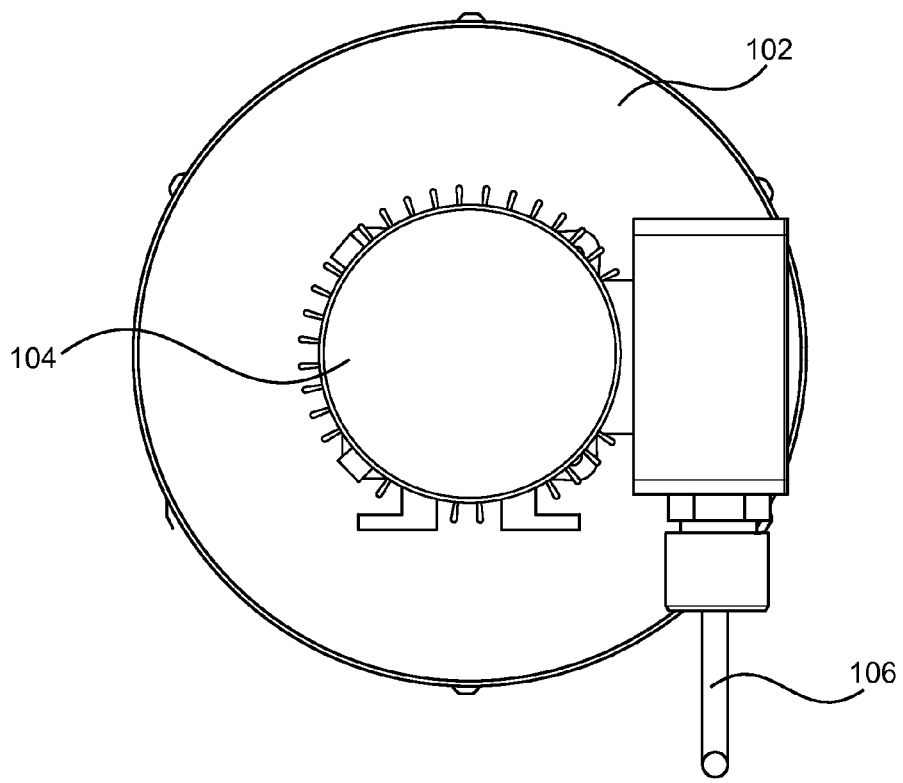

FIG. 5A-5B illustrates a front view and a rear view of the spiral magnetic therapeutic device 100 according to the preferred embodiment of the present invention. The safety sleeve 102 of the magnetic therapeutic device 100 is substantially hollow and cylindrical in shape. The electric motor 104 is connected to the safety sleeve 102 by means of the safety sleeve mount 108. The electric motor 104 of the device 100 can be powered by an AC supply or a DC supply. When the power supply 106 is turned on, the spiral magnetic therapeutic device 100 produces an oscillating magnetic field that increases the body's ability to work with less stresses and enhances the ability to heal and work efficiently.

Figure 6:
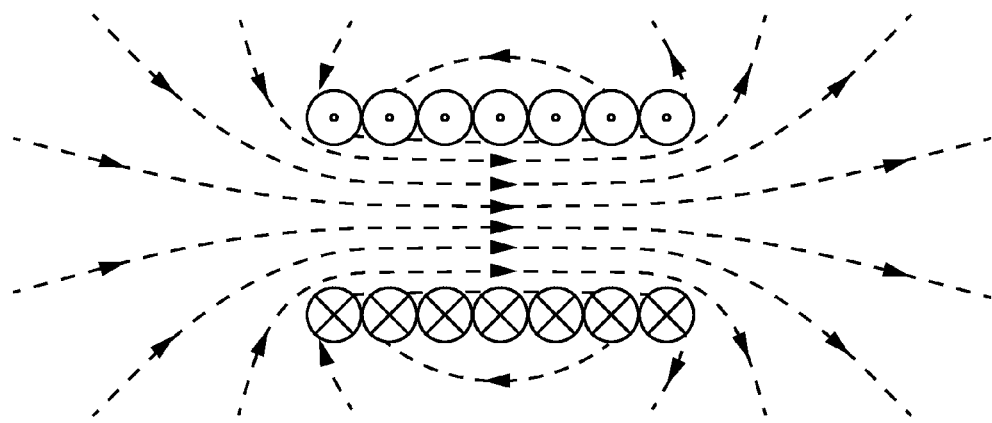
FIG. 6 illustrates a schematic image of magnetic fields generated by the spiral magnetic therapeutic device according to the preferred embodiment of the present invention.

FIG. 6 illustrates a schematic representation of magnetic fields generated by the spiral magnetic therapeutic device 100 according to the preferred embodiment of the present invention. The design of the present invention is predicated on the helical arrangement of the plurality of permanent magnets 118 at a certain angle or twist that generates a magnetic field of approximately 140 tesla that creates a vortex around the matter within a space. The magnetic field puts a positive and negative charge around matter at a cellular level, causing matter to fall into designed or proper realignment. The present invention creates a more subtle, stable, and natural magnetic field that increases the body's ability to work with less stresses and enhances the ability to heal and work efficiently. The oscillating magnetic field can be utilized in conjunction with depression, wellness, anti-aging, and sports medicine, as well as a remedy for pain management, wound healing, autoimmune disorders, addiction, and anxiety. Furthermore, as it is understood that the subtle energies in the quantum field can control DNA activity, great promise is held for the present invention in the treatment of illnesses based on DNA repair-deficiency disorders and other DNA based illnesses. The oscillating magnetic field has the effect of increasing the number white blood cells (WBC), which are strong indicators of immune strength and an increased blood flow and circulation. This magnetic field can also be utilized to achieve a remission and cure of several cancers, including stage IV (metastatic) diagnosed carcinomas, blood-borne cancers (lymphoma and leukemia), autoimmune disease, Glaucoma and Agent Orange poisoning.

Figure 7A:
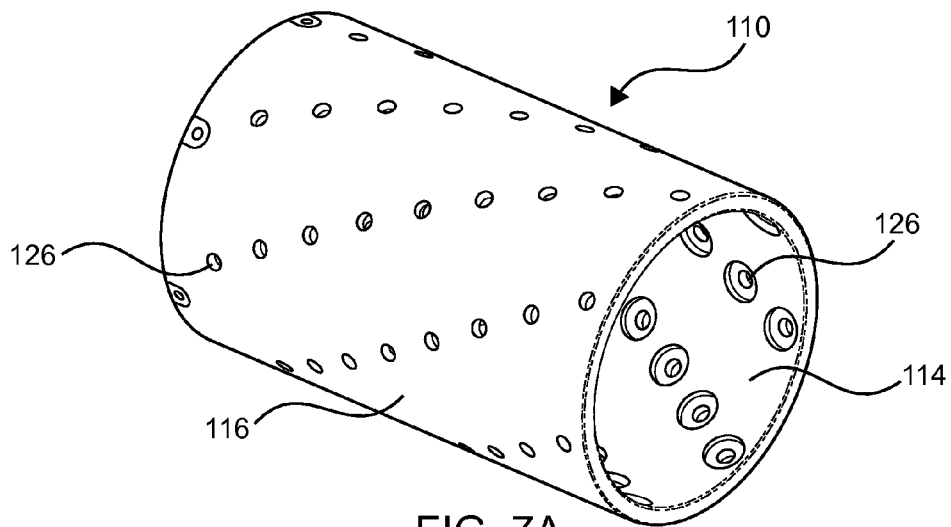
FIG. 7A illustrates a perspective view of the magnetic drum of the spiral magnetic therapeutic device according to the preferred embodiment of the present invention.
Figure 7B:
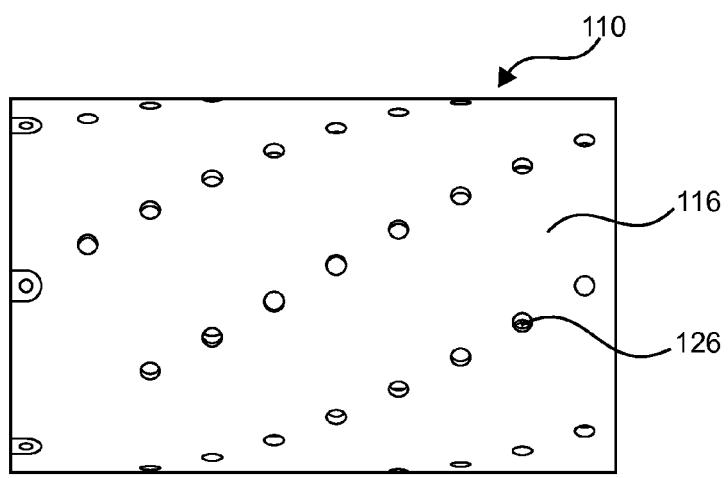
FIG. 7B illustrates a right side view of the magnetic drum of the spiral magnetic therapeutic device according to the preferred embodiment of the present invention.

FIGS. 7A-7B illustrate a perspective view and a right side view respectively of the magnetic drum 110 of the spiral magnetic therapeutic device 100 according to the preferred embodiment of the present invention. The magnetic drum 110 is substantially cylindrical in shape and has the plurality of slots 126 on the inner surface 114. The plurality of slots 126 are designed to form a helical pattern on the inner surface 114 of magnetic drum 110. The plurality of permanent magnets 118 being positioned or counter sunk on the plurality of slots 126 and forming a helical pattern, which once rotated is used to produce an oscillating magnetic field.

Although the invention has been shown and described with respect to certain embodiments, it is obvious that equivalent alterations and modifications will occur to others skilled in the art upon the reading and understanding of the specification. In particular, with regard to the various functions performed by the above-described components, the terms (including any reference to a "means") used to describe such components are intended to correspond, unless otherwise indicated, to any component which performs the specified function of the described component (e.g., that is functionally equivalent) even though not structurally equivalent to the disclosed component which performs the functions in the herein exemplary embodiments of the invention. In addition, while a particular feature of the invention may have been disclosed with respect to only one embodiment, such feature may be combined with one or more other features of other embodiments as may be desired or advantageous for any given or particular application.

I claim:

1. A magnetic therapeutic device, comprising:
   a safety sleeve affixed to an electric motor at a first end by means of a safety sleeve mount, the safety sleeve of substantially cylindrical shape with a second end closed;
   a magnetic drum substantially enclosed within the safety sleeve, wherein the magnetic drum comprises an inner surface and an outer surface, the magnetic drum connected to an output shaft of the electric motor by means of a plurality of bearings;
   a plurality of permanent magnets positioned in a plurality of slots formed in a helical pattern on the inner surface of the magnetic drum, the inner surface facing a central axis running longitudinally through the safety sleeve; and
   a power source connected to said electric motor;
   whereby the electric motor rotates the magnetic drum and the plurality of permanent magnets positioned thereon to produce an oscillating magnetic field thereby creating a magnetic vortex.

2. The magnetic therapeutic device of claim 1 wherein the plurality of permanent magnets is selected from the group consisting of neodymium (Nd2Fe14B), samarium-cobalt (SmCo5), Alnico, Sr-ferrite, and Sm(Co, Fe, Cu, Zr) magnets.

3. The magnetic therapeutic device of claim 1 wherein each of the plurality of permanent magnets has a north pole facing the central axis.

4. The magnetic therapeutic device of claim 1 wherein each of the plurality of permanent magnets has a south pole facing the central axis.

5. The magnetic therapeutic device of claim 1 wherein each of the plurality of permanent magnets has a remanence value of at least 0.5 T.

6. The magnetic therapeutic device of claim 1 wherein each of the plurality of permanent magnets has a remanence value of at least 0.7 T.

7. A device for magnetic therapy, comprising:
   a power source electrically connected to an electric motor comprising an output shaft;
   a safety sleeve of substantially cylindrical shape affixed to the electric motor by means of a safety sleeve mount;
   a magnetic drum substantially enclosed within the safety sleeve and having an inner surface and an outer surface, the magnetic drum connected to said output shaft by means of a plurality of bearings; and
   a plurality of permanent magnets positioned in a plurality of slots formed in a helical pattern on the inner surface of the magnetic drum;
   whereby the electric motor rotates the magnetic drum and the plurality of permanent magnets positioned thereon to produce an oscillating magnetic field.

8. The device for magnetic therapy according to claim 7 wherein the plurality of permanent magnets is selected from the group consisting of: neodymium (Nd2Fe14B), samarium-cobalt (SmCo5), Alnico, Sr-ferrite, and Sm(Co, Fe, Cu, Zr) magnets.

9. The device for magnetic therapy according to claim 7 wherein the inner surface of the magnetic drum faces a central axis running longitudinally through the safety sleeve.

10. The magnetic therapeutic device of claim 9 wherein each of the plurality of permanent magnets has a north pole facing the central axis.

11. The magnetic therapeutic device of claim 9 wherein each of the plurality of permanent magnets has a south pole facing the central axis.

12. The magnetic therapeutic device of claim 7 wherein each of the plurality of permanent magnets has a remanence value of at least 0.5 T.

13. The magnetic therapeutic device of claim 7 wherein each of the plurality of permanent magnets has a remanence value of at least 0.7 T.

14. A magnetic device for magnetic therapy, the device comprising:
   a magnetic drum having an inner surface and an outer surface;
   a plurality of permanent magnets positioned in a plurality of slots formed in a helical pattern on the inner surface of the magnetic drum;
   a substantially cylindrical safety sleeve surrounding said magnetic drum;
   an electric motor attached to the safety sleeve by means of a safety sleeve mount, the electric motor comprising an output shaft connected to said magnetic drum by means of a plurality of bearings; and
   a power source connected to said electric motor;
   whereby the electric motor rotates the magnetic drum and the plurality of permanent magnets positioned thereon to produce an oscillating magnetic field.

15. The magnetic device according to claim 14 wherein the plurality of permanent magnets is selected from the group consisting of: neodymium (Nd2Fe14B), samarium-cobalt (SmCo5), Alnico, Sr-ferrite, and Sm(Co, Fe, Cu, Zr) magnets.

16. The magnetic device according to claim 14 wherein the plurality of permanent magnets faces a central axis running longitudinally through the safety sleeve.

17. The magnetic therapeutic device of claim 16 wherein each of the plurality of permanent magnets has a north pole facing the central axis.

18. The magnetic therapeutic device of claim 16 wherein each of the plurality of permanent magnets has a south pole facing the central axis.

19. The magnetic therapeutic device of claim 14 wherein each of the plurality of permanent magnets has a remanence value of at least 0.5 T.

20. The magnetic therapeutic device of claim 14 wherein each of the plurality of magnets has a remanence value of at least 0.7 T.

* * * * *